US006835786B2

(12) United States Patent
Ishii et al.

(10) Patent No.: US 6,835,786 B2
(45) Date of Patent: Dec. 28, 2004

(54) (METH)ACRYLATE COMPOUND AND CURED PRODUCT THEREOF

(75) Inventors: Kenji Ishii, Tokyo (JP); Yasumasa Norisue, Tokyo (JP); Daisuke Ohno, Tokyo (JP); Makoto Miyamoto, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/626,575

(22) Filed: Jul. 25, 2003

(65) Prior Publication Data

US 2004/0132941 A1 Jul. 8, 2004

(30) Foreign Application Priority Data

Jul. 25, 2002 (JP) ........................................ 2002/216725
Aug. 5, 2002 (JP) ........................................ 2002/227622
Jun. 12, 2003 (JP) ........................................ 2003/168237

(51) Int. Cl.$^7$ ............................................. C08G 65/48
(52) U.S. Cl. ..................... 525/397; 525/391; 528/87; 528/421; 568/630; 568/631; 568/671
(58) Field of Search ................................ 525/391, 397; 528/87, 421; 568/630, 631, 671

(56) References Cited

U.S. PATENT DOCUMENTS 6,689,920 B2 * 2/2004 Ishii et al. .................. 568/638

FOREIGN PATENT DOCUMENTS

JP 2003-252833 * 9/2003
JP 2004-67817 * 3/2004

OTHER PUBLICATIONS

Ishii et al. 2003/0194562 A1, Oct. 16, 2003.*

* cited by examiner

*Primary Examiner*—Helen L. Pezzuto
(74) *Attorney, Agent, or Firm*—Wenderoth, Lind & Ponack, L.L.P.

(57) ABSTRACT

There are provided a polyfunctional (meth)acrylate compound which has the excellent properties of polyphenylene ether and is excellent in heat resistance and electric characteristics and excellent in reactivity by introducing a polyfunctional (meth)acrylate group into a bifunctional polyphenylene ether oligomer, and a cured product thereof which has a high glass transition temperature and has a low dielectric constant and a low dielectric loss tangent.

9 Claims, No Drawings

(METH)ACRYLATE COMPOUND AND CURED PRODUCT THEREOF

FIELD OF THE INVENTION

The present invention relates to a novel (meth)acrylate compound having a polyphenylene ether (to be sometimes referred to as "PPE" hereinafter) skeleton, a curable resin composition containing the above compound and a cured product thereof. The (meth)acrylate compound of the present invention can provide a polymer material excellent in heat resistance and dielectric characteristics by polymerizing the (meth)acrylic compound itself or copolymerizing the (meth)acrylic compound and a different unsaturated compound. Further, a photosensitive resin composition can be obtained by combining the (meth)acrylate compound of the present invention with a photopolymerization initiator. Such a photosensitive resin composition can be widely used for various applications such as a resin for a resist, a resin for a builup wiring board, a resin for sealing a liquid-crystal display panel, a resin for a color filter of a liquid crystal, a UV coating composition, various coating agents and an additive.

PRIOR ARTS OF THE INVENTION

Conventionally, (meth)acrylate compounds are widely used as a raw material for various functional polymer materials such as a photosensitive material, an optical material, a dental material, an electronic material and crosslinking agents for various polymers. However, since higher performances are required in these application fields in recent years, physical properties required as a functional polymer material become severer increasingly. As such physical properties, for example, heat resistance, weather resistance, low moisture absorptivity, high refractive index, high fracture toughness, low dielectric constant and low dielectric loss tangent are required, as disclosed in JP-A-11-214815. Until now, these required physical properties have not been completely satisfied.

SUMMARY OF THE INVENTION

It is an object of the present invention to provide a novel (meth)acrylate compound having excellent heat resistance and having a low dielectric constant and a low dielectric loss tangent, a curable resin composition containing the above compound and a cured product thereof.

The present invention provides a (meth)acrylate compound represented by the formula (1) or the formula (2),

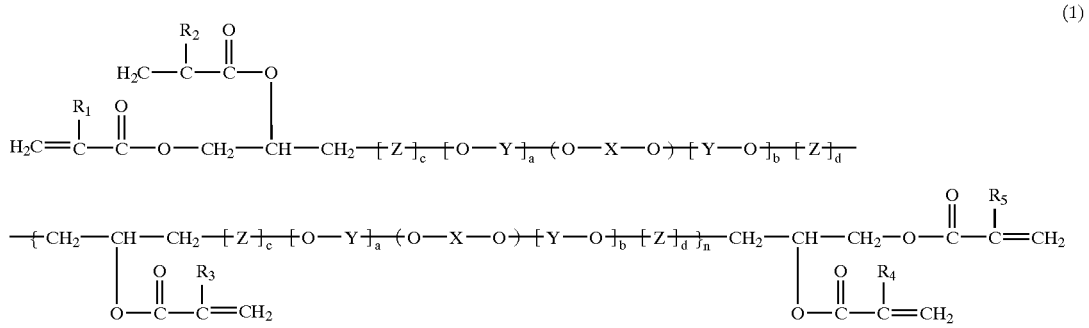

(1)

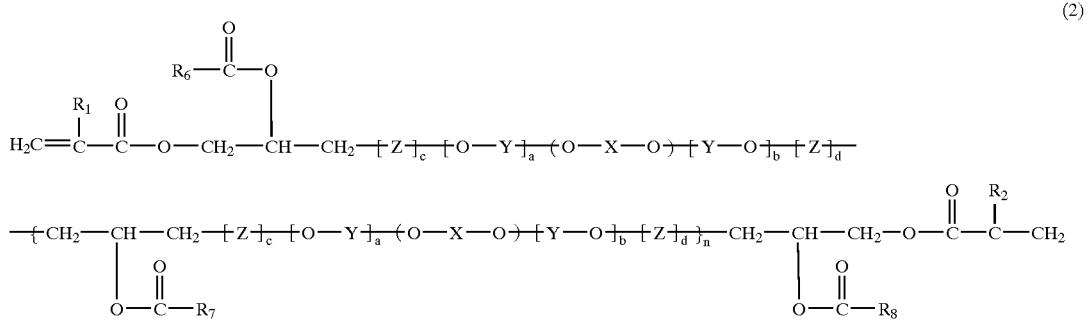

(2)

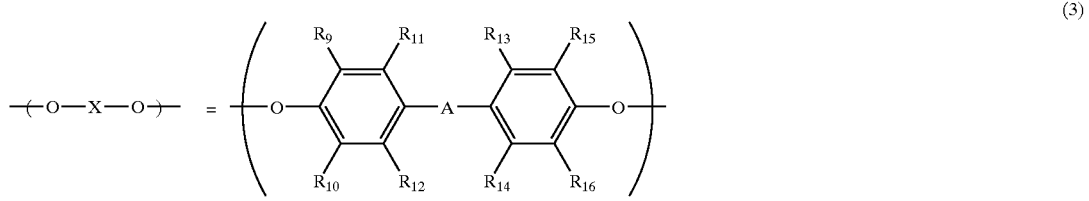

(3)

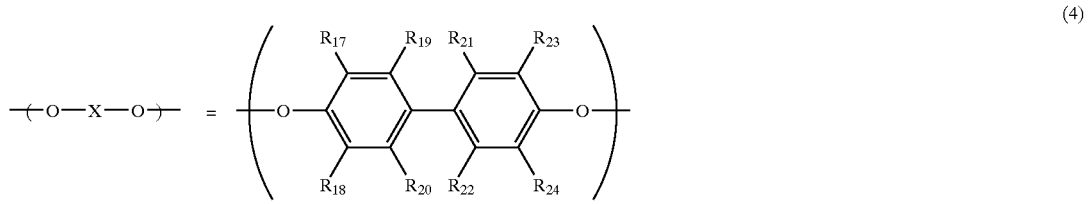

(4)

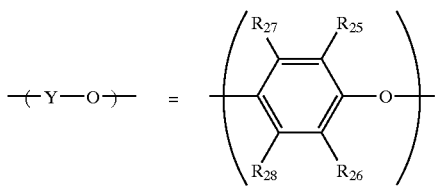

(5)

wherein each of $R_1$, $R_2$, $R_3$, $R_4$ and $R_5$ is independently a hydrogen atom or a methyl group, each of $R_6$, $R_7$ and $R_8$ is independently a linear, branched or cyclic hydrocarbon having or less carbon atoms, —(O—X—O)— is represented by the formula (3) (in which A is a linear, branched or cyclic hydrocarbon having 20 or less carbon atoms, each of $R_9$, $R_{10}$, $R_{15}$ and $R_{16}$ is independently a halogen atom, an alkyl group having 6 or less carbon atoms or a phenyl group and each of $R_{11}$, $R_{12}$, $R_{13}$ and $R_{14}$ is independently a hydrogen atom, a halogen atom, an alkyl group having 6 or less carbon atoms or a phenyl group) or the formula (4) (in which each of $R_{17}$, $R_{18}$, $R_{19}$ $R_{23}$ and $R_{24}$ is independently a halogen atom, an alkyl group having 6 or less carbon atoms or a phenyl group and each of $R_{20}$, $R_{21}$ and $R_{22}$ is independently a hydrogen atom, a halogen atom, an alkyl group having 6 or less carbon atoms or a phenyl group), —(Y—O)— is an arrangement of one kind of structure defined by the formula (5) or a random arrangement of at least two kinds of structures defined by the formula (5) (in which each of $R_{25}$ and $R_{26}$ is independently a halogen atom, an alkyl group having 6 or less carbon atoms or a phenyl group, and each of $R_{27}$ and $R_{28}$ is independently a hydrogen atom, a halogen atom, an alkyl group having 6 or less carbon atoms or a phenyl group), Z is an organic group which has at least one carbon atom and which may contain an oxygen atom, a nitrogen atom, a sulfur atom or a halogen atom, Z is preferably an organic group which has 1 to 10 carbon atoms and which may contain an oxygen atom, each of a and b is an integer of 0 to 30, provided that at least either a or b is not 0, each of c and d is an integer of 0 or 1, and n is an integer of 0 to 10.

The present invention further provides a curable resin composition containing the above (meth)acrylate compound.

The present invention further provides a cured product obtained by curing the above curable resin composition.

DETAILED DESCRIPTION OF THE INVENTION

The present inventors have disclosed a bifunctional PPE oligomer having the excellent dielectric characteristics and heat resistance of PPE (Japanese patent application No. 2001-196569). Further, the present inventors have disclosed an epoxy (meth)acrylate compound obtained by imparting radical polymerizability to the above oligomer (JP-A-2001-387968) and a (meth)acrylate compound (Japanese patent application No. 2002-053653). As a result of further diligent studies, the present inventors have found that the object is satisfied by introducing at least two radical polymerizable (meth)acrylate groups into an oligomer compound of a bifunctional PPE (in which —(O—X—O)— is represented by the formula (3) or the formula (4) and —(Y—O)— is an arrangement of one kind of structure defined by the formula (5) or a random arrangement of at least two kinds of structures defined by the formula (5)). Thus, the present inventors have completed the present invention. That is, the present invention relates to a (meth)acrylate compound represented by the formula (1) or the formula (2).

Of compounds represented by the formula (1) or the formula (2), provided by the present invention, a preferred compound is a (meth)acrylate compound in which, in —(O—X—O)— of the formula (3), $R_9$, $R_{10}$, $R_{15}$ and $R_{16}$ are an alkyl group having 3 or less carbon atoms, $R_{11}$, $R_{12}$, $R_{13}$ and $R_{14}$ are a hydrogen atom or an alkyl group having 3 or less carbon atoms, in —(O—X—O)— of the formula (4), $R_{17}$, $R_{18}$, $R_{19}$, $R_{23}$ and $R_{24}$ are an alkyl group having 3 or less carbon atoms, $R_{20}$, $R_{21}$ and $R_{22}$ are a hydrogen atom or an alkyl group having 3 or less carbon atoms, and, in —(Y—O)— of the formula (5), $R_{25}$ and $R_{26}$ are an alkyl group having 3 or less carbon atoms and $R_{27}$ and $R_{28}$ are a hydrogen atom or an alkyl group having 3 or less carbon atoms.

More preferred is a (meth)acrylate compound in which, in —(O—X—O)— of the formula (3), $R_9$, $R_{10}$, $R_{15}$ and $R_{16}$ are a methyl group, $R_{11}$, $R_{12}$, $R_{13}$ and $R_{14}$ are a hydrogen atom or a methyl group, in —(O—X—O)— of the formula (4), $R_{17}$, $R_{18}$, $R_{19}$, $R_{23}$ and $R_{24}$ are a methyl group, $R_{20}$, $R_{21}$, and $R_{22}$ are a hydrogen atom or a methyl group, and, in —(Y—O)— of the formula (5), $R_{25}$ and $R_{26}$ are a methyl group and $R_{27}$ and $R_{28}$ are a hydrogen atom or a methyl group.

In the above formula (1) or (2), Z is preferably an organic group having 1 to 10 carbon atoms which group may contain an oxygen atom. More specifically, for example, —O—[Z]— is —O—[(CH2)n]—, —O—[(CH2)m—O—CH2]—, or

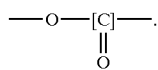

A is preferably a linear, branched or cyclic hydrocarbon having 15 or less carbon atoms. More specifically, it includes the following examples.

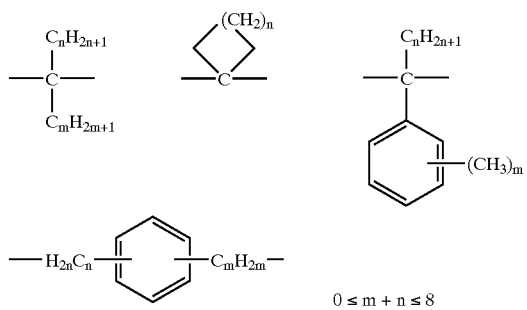

The process for producing the (meth)acrylate compound of the formula (1) or the formula (2) of the present invention is not specially limited and it may be produced by any methods. For example, it can be obtained by reacting a compound represented by the formula (9) with a (meth)acrylic acid or a (meth)acrylic acid derivative. Concretely, first, the compound of the formula (9) is reacted with a (meth)acrylic acid in the presence of a compound as a catalyst. The above compound includes, for example, amines such as triethylamine, dimethylbutylamine and tri-n-butylamine, quaternary ammonium salts such as tetramethylammonium salt, tetraethyl ammonium salt, tetrabutylammonium salt and benzyltriethyl ammonium salt, quaternary phosphonium salts, phosphines such as triphenylphosphine, and imidazoles such as 2-methylimidazole and 2-ethyl-4-methylimidazole.

Then, an obtained product is reacted with a carboxylic acid at a temperature of, preferably, 70° C. to 150° C. in the presence of an esterification catalyst such as p-toluenesulfonic acid, trifluoromethanesulfonic acid or sulfuric acid and preferably in the presence of a solvent such as toluene, xylene, cyclohexane, n-hexane, n-heptene or mixtures of these. Otherwise, the obtained product is reacted with a carbonyl chloride at a temperature of −20° C. to 50° C. in the presence of, for example, an organic amine, sodium hydroxide or sodium carbonate and preferably in the presence of a solvent such as toluene, xylene, cyclohexane, n-hexane, n-heptene, methylene chloride, chloroform or mixtures of these. As a result, an intended compound can be obtained.

epichlorohydrin and a bifunctional PPE oligomer obtained by a method, in which a bivalent phenol and a monovalent phenol are oxidized and polymerized, disclosed in Japanese patent application No. 2002-018508.

Then, the curable resin composition of the present invention will be explained. The above curable resin composition is characterized in that it contains the above-described (meth)acrylate compound of the present invention. The curable resin composition may contain a known epoxy resin, an oxetane resin, a compound having a polymerizable unsaturated group, photopolymerization and/or thermal-polymerization initiators, a photosensitizer, or the like.

The epoxy resin can be selected from generally known epoxy resins. Examples thereof include a bisphenol A type epoxy resin, a bisphenol F type epoxy resin, a biphenyl type epoxy resin, a phenol novolak type epoxy resin, a cresol novolak type epoxy resin, a xylene novolak type epoxy resin, triglycidyl isocyanurate, an alicyclic epoxy resin, a dicyclopentadiene novolak type epoxy resin, a biphenyl novolak type epoxy resin and epoxy resins having a PPE structure disclosed in Japanese patent application Nos. 2001-353194 and 2002-018508. These epoxy resins may be used alone or in combination.

The oxetane resin can be selected from generally known oxetane resins. Examples of the oxetane resin include alkyl

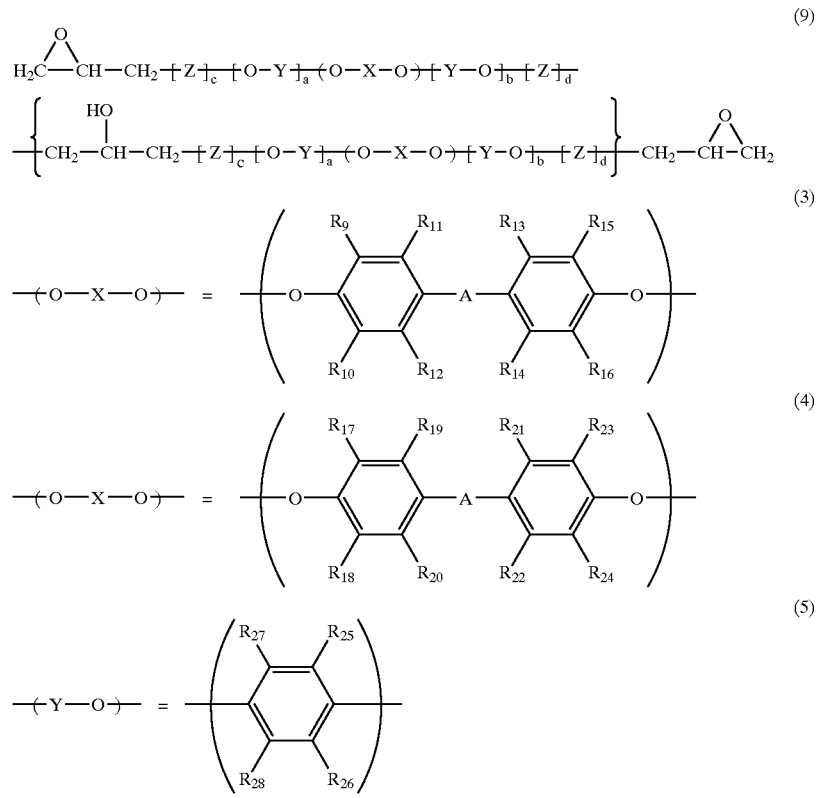

In the above formulae, Z, a, b, c, d and n in the formula (9) are as defined in the formula (1) or (2) and each of the other symbols is as defined in each formula shown before.

The compound of the formula (9) can be obtained by a method disclosed in Japanese patent application No. 2001-353194. Otherwise, it can be obtained by reaction between oxetanes such as oxetane, 2-methyloxetane, 2,2-dimethyloxetane, 3-methyloxetane and 3,3-dimethyloxetane, 3-methyl-3-methoxymethyloxetane, 3,3'-bis(trifluoromethyl) perfluorooxetane, 2-chloromethyloxetane, 3,3-bis (chloromethyl) oxetane, OXT-101 (trade name, supplied by TOAGOSEI Co., Ltd.)

and OXT-121 (trade name, supplied by TOAGOSEI Co., Ltd.). These oxetane resins may be used alone or in combination.

When the epoxy resin and/or the oxetane resin are used in the curable resin composition of the present invention, an epoxy resin curing agent and/or an oxetane resin curing agent can be used. The epoxy resin curing agent is selected from generally known curing agents. Examples of the epoxy resin curing agent include imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole and 2-phenyl-4-methyl-5-hydroxymethylimidazole; amine compounds such as dicyandiamide, benzyldimethylamine, 4-methyl-N,N-dimethylbenzylamine, diaminodiphenylmethane and diaminodiphenylsulfone; and phosphine compounds such as phosphonium compounds. The oxetane resin curing agent can be selected from known cationic polymerization initiators. Commercially available examples include SAN-AID SI-60L, SAN-AID SI-80L, SAN-AID SI-100L (supplied by Sanshin Chemical Industry Co., Ltd.), CI-2064 (supplied by Nippon Soda Co., Ltd.), IRGACURE261 (supplied by Ciba Specialty Chemicals), ADEKAOPTMER SP-170, ADEKAOPTMER SP-150, (supplied by Asahi Denka Kogyo K.K.), and CYRACURE UVI-6990 (supplied by Union Carbide Corporation). The cationic polymerization initiators can be used as an epoxy resin curing agent. These curing agents may be used alone or in combination.

The compound having a polymerizable unsaturated group can be selected from generally known compounds having a polymerizable unsaturated group. Examples thereof include (meth)acrylates of monohydric and polyhydric alcohols such as 2-hydroxyethyl(meth)acrylate, 2-hydroxypropyl (meth)acrylate, polypropylene glycol di(meth)acrylate, trimethylol propane di(meth)acrylate, trimethylol propane tri (meth)acrylate, pentaerythritol tetra(meth)acrylate and dipentaerythritol hexa(meth)acrylate, epoxy (meth)acrylates such as a bisphenol A type epoxy (meth)acrylate, a bisphenol F type epoxy (meth)acrylate and epoxy (meth)acrylates having a PPE structure disclosed in Japanese patent application Nos. 2001-387968 and 2002-038156, (meth)acrylates having a PPE skeleton disclosed in Japanese patent application Nos. 2002-053653, 2002-055765, 2002-216725 and 2002-227622 and and a benzocyclobutene resin. These compounds having a polymerizable unsaturated group may be used alone or in combination.

The photopolymerization initiator can be selected from generally known photopolymerization initiators. Examples of the photopolymerization initiator include α-diketones such as benzyl and diacetyl, acyloin ethers such as benzoyl ethyl ether and benzoin isopropyl ether, thioxanthones such as thioxanthone, 2,4-diethylthioxanthone and 2-isopropylthioxanthone, benzophenones such as benzophenone and 4,4'-bis(dimethylamino)benzophenone, acetophenones such as acetophenone, 2,2'-dimethoxy-2-phenylacetophenone and β-methoxy acetophenone, and aminoacetophenones such as 2-methyl-1-[4-(methylthio) phenyl]-2-morpholinopropane-1-one and 2-benzyl-2-dimethylamino-1-(-4-morpholinophenyl)-butanone-1. These photopolymerization initiators are used alone or in combination.

Further, the photopolymerization initiator may be used in combination with one kind of or at least two kinds of known photosensitizer(s). Examples of the photosensitizer include N,N-dimethylaminoethylbenzoate, N,N-dimethylaminoisoamylbenzoate, triethanolamine and triethylamine.

The thermal polymerization initiator maybe selected from generally known thermal polymerization initiators. Examples thereof include peroxides such as benzoyl peroxide, p-chlorobenzoyl peroxide, di-t-butylperoxide, diisopropyl peroxycarbonate and di-2-ethylhexylperoxycarbonate, and azo compounds such as azobisisobutylonitrile.

Further, when the curable resin composition of the present invention is produced, there may be added a known additive such as an inorganic filler, a color pigment, an antifoamer, a surface conditioner, a flame retardant, an ultraviolet absorber, an antioxidant, a polymerization inhibitor or a flow regulator, as required. Examples of the inorganic filler include silicas such as natural silica, fused silica and amorphous silica, white carbon, titanium white, aerosil, alumina, talc, natural mica, synthetic mica, kaolin, clay, aluminum hydroxide, barium sulfate, E-glass, A-glass, C-glass, L-glass, D-glass, S-glass and M-glass G20. The thus-obtained curable resin composition is useful for various applications such as a solder resist composition, buildup wiring board materials, insulating coatings, adhesives, printing inks and coating agents.

The cured product of the present invention can be obtained by curing the curable resin composition of the present invention, obtained by the above method, according to a known curing method such as a curing method using an electron beam, ultraviolet light or heat. When ultraviolet light is used for the curing, there may be used a low-pressure mercury lamp, an intermediate-pressure mercury lamp, a high-pressure mercury lamp, an ultrahigh-pressure mercury lamp, a xenon lamp, a metal halide lamp, or the like, as a light source for ultraviolet light.

EFFECT OF THE INVENTION

The polyfunctional (meth)acrylate compound of the present invention has a higher glass transition temperature than a bisphenol A type epoxy acrylate or a novolak type epoxy acrylate and it has a low dielectric constant and a low dielectric loss tangent. Therefore, the (meth)acrylate compound of the present invention is remarkably useful as a high-functional polymer material and can be used, as a thermally and electrically excellent material, for wide applications such as various coating agents, UV coating compositions, additives, resists and buildup wiring board materials.

EXAMPLE

The present invention will be explained concretely with reference to Examples and Comparative Examples, while the present invention shall not be specially limited to these Examples. A number average molecular weight and a weight average molecular weight were measured according to the gel permeation chromatography (GPC) method. Data processing was carried out according to the GPC curve and molecular weight calibration curve of a sample. The molecular weight calibration curve was obtained by making an approximation of a relation between the molecular weight of a standard polystyrene and the dissolution time thereof with the following equation, $$\mathrm{Log} M = A_0 X^3 + A_1 X^2 + A_2 X + A_3 + A_4 / X^2$$

wherein M: a molecular weight, X: an elution time-19 minutes, and A: a coefficient.

Further, a peak derived from benzoic acid was confirmed at 7.4–8.2 ppm by a $^1$H-NMR analysis. A hydroxyl group equivalent was determined from an absorption intensity at 3,600 cm$^{-1}$ in an IR analysis (solution cell method; cell length=1 mm) using 2,6-dimethylphenol as a standard reference material and using dry methylene chloride as a solvent.

Example 1

(Synthesis of Bifunctional PPE Oligomer Compound)

A longitudinally long reactor having a volume of 5 liters and equipped with a stirrer, a thermometer, an air-introducing tube and baffleplates was charged with 3.3 g (0.030 mol) of CuCl, 176.8 g (1.34 mol) of di-n-butylamine and 1,000 g of methyl ethyl ketone. The components were stirred at a reaction temperature of 40° C. A solution of 108.0 g (0.40 mol) of 2,2',3,3',5,5'-hexamethyl-[1,1'-biphenyl]-4, 4'-diol as a bivalent phenol and 146.5 g (1.20 mol) of 2,6-dimehtylphenol in 2,000 g of methyl ethyl ketone was dropwise added to the reactor over 120 minutes while carrying out bubbling with 5L/min of air. After the completion of the addition, stirring was carried out for 60 minutes while continuing the bubbling with 5L/min of air. A disodium dihydrogen ethylenediamine tetraacetate aqueous solution was added to the stirred mixture to terminate the reaction. Then, washing was carried out with 1N hydrochloric acid aqueous solution and then washing was carried out with pure water. The thus-obtained solution was concentrated by an evaporator and then dried under reduced pressure, to obtain 241.8 g of a bifunctional phenylene ether oligomer. The oligomer had a number average molecular weight of 810, a weight average molecular weight of 1,105 and a hydroxyl group equivalent of 475.

(Synthesis of Epoxy Compound)

A reactor equipped with a stirrer, a thermometer and a dropping funnel was heated up to 100° C. and charged with 200 g (hydroxyl group 0.44 mol) of the above oligomer and 1,168 g of epichlorohydrin. Then, a solution obtained by dissolving 34.4 g (0.52 mol) of sodium ethoxide in 120 g of ethanol was dropwise added from the dropping funnel over 60 minutes. After the completion of the addition, stirring was carried out for 5 hours. Then, washing was carried out with pure water and further a filtration was carried out, to remove a generated salt and impurities. Excess epichlorohydrin was distilled off from the obtained solution, and drying under reduced pressure was carried out, to obtain 212.8 g of an epoxy compound represented by the formula (9). According to an IR analysis of the obtained epoxy compound, the absorption peak (3,600 cm-1) of a phenolichydroxyl group disappeared, and according to a NMR analysis, a peak derived from glycidyl ether appeared, so that it was confirmed that all functional groups were changed. The epoxy compound had a number average molecular weight of 965, a weight average molecular weight of 1,213 and an epoxy equivalent of 543.

(Synthesis of Epoxy Acrylate Compound)

A reactor equipped with a stirrer, a thermometer and a reflux tube was charged with 50 g of the above epoxy compound, 7.9 g of an acrylic acid, 40 g of toluene, 0.26 g of triethylamine and 26 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 80 g of toluene. The diluted solution was dropwise added to methanol to obtain a precipitate. A solid was recovered by a filtration and then the recovered solid was dried under reduced pressure to obtain 38.5 g of an epoxy acrylate compound. The epoxy acrylate compound had a number average molecular weight of 1,375 and a weight average molecular weight of 1,656.

(Synthesis of Polyfunctional Acrylate Compound)

A reactor equipped with a stirrer, a thermometer and a dropping funnel was charged with 25 g of the above epoxy acrylate compound, 5.4 g of triethylamine and 400 g of methylene chloride. 4.9 g of acryloyl chloride and 100 g of methylene chloride were placed in the dropping funnel. The mixture in the reactor was cooled down to 0° C. under a nitrogen atmosphere and the acryloyl chloride was dropwise added to the mixture over 1 hour with stirring. Then, the mixture was returned to room temperature and stirring was continued. The reaction mixture was sampled and the reaction was traced by a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 17.4 g of a polyfunctional acrylate compound represented by the formula (1). The polyfunctional acrylate compound had a number average molecular weight of 1,655 and a weight average molecular weight of 2,305.

Example 2

10 g of the same polyfunctional acrylate compound as that obtained in Example 1 was molten, degassed and molded at 150° C. and then thermally cured at 200° C. for 6 hours to obtain a cured product.

Example 3

6 g of the same polyfunctional acrylate compound as that obtained in Example 1 was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 1,500 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Comparative Example 1

10 g of the same epoxy acrylate compound as that obtained in Example 1 was molten, degassed and molded at 150° C. and then thermally cured at 200° C. for 6 hours to obtain a cured product.

The cured products obtained in Example 2 and Comparative Example 1 were evaluated for properties by the following methods.

Glass transition temperature (Tg): determined according to a dynamic viscoelasticity measurement (DMA). The measurement was carried out at an oscillation frequency of 10 Hz.

Dielectric constant and dielectric loss tangent: determined according to a cavity resonant oscillation method.

Table 1 shows evaluation results of the above physical properties.

TABLE 1

|  | Example 2 | Comparative Example 1 |
|---|---|---|
| Tg (° C.) | 237 | 198 |
| Dielectric constant (1 GHz) | 2.66 | 2.74 |
| Dielectric loss tangent (1 GHz) | 0.009 | 0.018 |

Example 4
(Synthesis of Bifunctional PPE Oligomer Compound)

A longitudinally long reactor having a volume of 2 liters and equipped with a stirrer, a thermometer, an air-introducing tube and baffleplates was charged with 1.3 g (0.012 mol) of CuCl, 70.7 g (0.55 mol) of di-n-butylamine and 400 g of methyl ethyl ketone. The components were stirred at a reaction temperature of 40° C. A solution of 45.4 g (0.16 mol) of 4,4'-(1-methylethylidene)bis(2,6-dimethylphenol) as a bivalent phenol and 58.6 g (0.48 mol) of 2,6-dimethylphenol in 800 g of methyl ethyl ketone was dropwise added to the mixture in the reactor over 120 minutes while carrying out bubbling with 2L/min of air. After the completion of the addition, stirring was carried out for 60 minutes while continuing the bubbling with 2L/min of air. A disodium dihydrogen ethylenediamine tetraacetate aqueous solution was added to the stirred mixture to terminate the reaction. Then, washing was carried out with 1N hydrochloric acid aqueous solution and then washing was carried out with pure water. The thus-obtained solution was concentrated by an evaporator and then dried under reduced pressure, to obtain 98.8 g of a bifunctional phenylene ether oligomer. The oligomer had a number average molecular weight of 845, a weight average molecular weight of 1,106 and a hydroxyl group equivalent of 451.

(Synthesis of Epoxy Compound)

A reactor equipped with a stirrer, a thermometer and a dropping funnel was heated up to 100° C. and charged with 49.6 g (hydroxyl group 0.11 mol) of the above oligomer and 292 g of epichlorohydrin. Then, a solution obtained by dissolving 8.6 g (0.13 mol) of sodium ethoxide in 30 g of ethanol was dropwise added from the dropping funnel over 60 minutes. After the completion of the addition, stirring was further carried out for 5 hours. Then, washing was carried out with pure water and further a filtration was carried out, to remove a generated salt and impurities. Excess epichlorohydrin was distilled off from the obtained solution, and drying under reduced pressure was carried out, to obtain 53.6 g of an epoxy compound represented by the formula (9). According to an IR analysis of the obtained epoxy compound, the absorption peak (3,600 cm-1) of a phenolic hydroxyl group disappeared, and according to a NMR analysis, a peak derived from glycidyl ether appeared, so that it was confirmed that all functional groups were changed. The epoxy compound had a number average molecular weight of 998, a weight average molecular weight of 1,277 and an epoxy equivalent of 565.

(Synthesis of Epoxy Acrylate Compound)

A reactor equipped with a stirrer, a thermometer and a reflux tube was charged with 26 g of the above epoxy compound, 3.3 g of an acrylic acid, 20 g of toluene, 0.13 g of triphenylphosphine and 13 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 40 g of toluene. The diluted reaction solution was dropwise added to methanol to obtain a precipitate. A solid was recovered by a filtration and then the recovered solid was dried under reduced pressure to obtain 26.4 g of an epoxy acrylate compound. The epoxy acrylate compound had a number average molecular weight of 1,388 and a weight average molecular weight of 1,679.

(Synthesis of Polyfunctional Acrylate Compound)

A reactor equipped with a stirrer, a thermometer and a dropping funnel was charged with 25 g of the above epoxy acrylate compound, 5.2 g of triethylamine and 400 g of methylene chloride. 4.6 g of acryloyl chloride and 100 g of methylene chloride were placed in the dropping funnel. The mixture in the reactor was cooled down to 0° C. under nitrogen atmosphere and the acryloyl chloride was dropwise added to the mixture over 1 hour with stirring. Then, the mixture was returned to room temperature and stirring was continued. The reaction was traced by sampling the reaction mixture and carrying out a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 17.6 g of a polyfunctional acrylate compound represented by the formula (1). The polyfunctional acrylate compound had a number average molecular weight of 1,664 and a weight average molecular weight of 2,205.

10 g of the polyfunctional acrylate compound was molten, degassed and molded at 150° C. and then cured at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 2,000 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Example 5
(Synthesis of Bifunctional PPE Oligomer Compound)

A longitudinally long reactor having a volume of 2 liters and equipped with a stirrer, a thermometer, an air-introducing tube and baffleplates was charged with 1.3 g (0.012 mol) of CuCl, 70.7 g (0.55 mol) of di-n-butylamine and 400 g of methyl ethyl ketone. The components were stirred at a reaction temperature of 40° C. A solution of 51.8 g (0.16 mol) of 4,4'-cyclohexylidenebis(2,6-dimethylphenol) as a bivalent phenol and 58.6 g (0.48 mol) of 2,6-dimehtylphenol in 800 g of methyl ethyl ketone was dropwise added to the mixture in the reactor over 120 minutes while carrying out bubbling with 2L/min of air. After the completion of the addition, stirring was carried out for 60 minutes while continuing the bubbling with 2L/min of air. A disodium dihydrogen ethylenediamine tetraacetate aqueous solution was added to the stirred mixture to terminate the reaction. Then, washing was carried out with 1 N hydrochloric acid aqueous solution and then washing was carried out with pure water. The thus-obtained solution was concentrated by an evaporator and then dried under reduced pressure, to obtain 102.6 g of a bifunctional phenylene ether oligomer. The oligomer had a number average molecular weight of 877, a weight average molecular weight of 1,183 and a hydroxyl group equivalent of 477.

(Synthesis of Epoxy Compound)

A reactor equipped with a stirrer, a thermometer and a dropping funnel was heated up to 100° C. and charged with 52.5 g (hydroxyl group 0.11 mol) of the above oligomer and 292 g of epichlorohydrin. Then, a solution obtained by dissolving 8.6 g (0.13 mol) of sodium ethoxidein 30 g of ethanol was dropwise added from the dropping funnel over 60 minutes. After the completion of the addition, stirring was further carried out for 5 hours. Then, washing was carried out with pure water, and further a filtration was carried out, to remove a generated salt and impurities. Excess epichlorohydrin was distilled off from the obtained solution, and drying under reduced pressure was carried out, to obtain 54.1 g of an epoxy compound represented by the formula (9). According to an IR analysis of the obtained epoxy compound, the absorption peak (3,600 cm-1) of a phenolic hydroxyl group disappeared, and according to a NMR analysis, a peak derived from glycidyl ether appeared, so that it was confirmed that all functional groups were changed. The epoxy compound had a number average molecular weight of 1,029, a weight average molecular weight of 1,301 and an epoxy equivalent of 576.

(Synthesis of Epoxy Acrylate Compound)

A reactor equipped with a stirrer, a thermometer and a reflux tube was charged with 26.5 g of the above epoxy compound, 3.3 g of an acrylic acid, 20 g of toluene, 0.13 g of triphenylphosphine and 13 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 40 g of toluene. The diluted reaction solution was dropwise added to methanol to obtain a precipitate. A solid was recovered by a filtration and then the recovered solid was dried under reduced pressure to obtain 26.5 g of an epoxy acrylate compound. The epoxy acrylate compound had a number average molecular weight of 1,411 and a weight average molecular weight of 1,721.

(Synthesis of Polyfunctional Acrylate Compound)

A reactor equipped with a stirrer, a thermometer and a dropping funnel was charged with 25 g of the above epoxy acrylate compound, 5.1 g of triethylamine and 400 g of methylene chloride. 4.5 g of acryloyl chloride and 100 g of methylene chloride were placed in the dropping funnel. The mixture in the reactor was cooled down to 0° C. under a nitrogen atmosphere and the acryloyl chloride was dropwise added to the mixture over 1 hour with stirring. Then, the mixture was returned to room temperature and stirring was continued. The reaction was traced by sampling the reaction mixture and carrying out a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 18.3 g of a polyfunctional acrylate compound represented by the formula (1). The polyfunctional acrylate compound had a number average molecular weight of 1,710 and a weight average molecular weight of 2,341.

10 g of the polyfunctional acrylate compound was molten, degassed and molded at 150° C. and then cured at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 2,000 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Example 6

(Synthesis of Bifunctional PPE Oligomer Compound)

A longitudinally long reactor having a volume of 2 liters and equipped with a stirrer, a thermometer, an air-introducing tube and baffleplates was charged with 1.3 g (0.012 mol) of CuCl, 70.7 g (0.55 mol) of di-n-butylamine and 400 g of methyl ethyl ketone. The components were stirred at a reaction temperature of 40° C. A solution of 45.4 g (0.16 mol) of 4,4'-methylidenebis(2,3,6-trimethylphenol) as a bivalent phenol and 58.6 g (0.48 mol) of 2,6-dimehtylphenol in 800 g of methyl ethyl ketone was dropwise added to the mixture in the reactor over 120 minutes while carrying out bubbling with 2L/min of air. After the completion of the addition, stirring was carried out for 60 minutes while continuing the bubbling with 2L/min of air. A disodium dihydrogen ethylenediamine tetraacetate aqueous solution was added to the stirred mixture to terminate the reaction. Then, washing was carried out with 1 N hydrochloric acid aqueous solution and then washing was carried out with pure water. The thus-obtained solution was concentrated by an evaporator and then dried under reduced pressure, to obtain 97.4 g of a bifunctional phenylene ether oligomer. The oligomer had a number average molecular weight of 852, a weight average molecular weight of 1,133 and a hydroxyl group equivalent of 460.

(Synthesis of Epoxy Compound)

A reactor equipped with a stirrer, a thermometer and a dropping funnel was heated up to 100° C. and charged with 50.6 g (hydroxyl group 0.11 mol) of the above oligomer and 292 g of epichlorohydrin. Then, a solution obtained by dissolving 8.6 g (0.13 mol) of sodium ethoxidein 30 g of ethanol was dropwise added from the dropping funnel over 60 minutes. After the completion of the addition, stirring was further carried out for 5 hours. Then, washing was carried out with pure water, and further a filtration was carried out, to remove a generated salt and impurities. Excess epichlorohydrin was distilled off from the obtained solution, and drying under reduced pressure was carried out, to obtain 53.8 g of an epoxy compound represented by the formula (9). According to an IR analysis of the obtained epoxy compound, the absorption peak (3,600 cm-1) of a phenolic hydroxyl group disappeared, and according to a NMR analysis, a peak derived from glycidyl ether appeared, so that it was confirmed that all functional groups were changed. The epoxy compound had a number average molecular weight of 1,005, a weight average molecular weight of 1,275 and an epoxy equivalent of 566.

(Synthesis of Epoxy Acrylate Compound)

A reactor equipped with a stirrer, a thermometer and a reflux tube was charged with 26 g of the above epoxy compound, 3.3 g of an acrylic acid, 20 g of toluene, 0.13 g of triphenylphosphine and 13 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 40 g of toluene. The diluted reaction solution was dropwise added to methanol to obtain a precipitate. A solid was recovered by a filtration and then the recovered solid was dried under reduced pressure to obtain 26.7 g of an epoxy acrylate compound. The epoxy acrylate compound had a number average molecular weight of 1,395 and a weight average molecular weight of 1,687.

(Synthesis of Polyfunctional Acrylate Compound)

A reactor equipped with a stirrer, a thermometer and a dropping funnel was charged with 25 g of the above epoxy acrylate compound, 5.2 g of triethylamine and 400 g of methylene chloride. 4.6 g of acryloyl chloride and 100 g of methylene chloride were placed in the dropping funnel. The mixture in the reactor was cooled down to 0° C. under nitrogen atmosphere and the acryloyl chloride was dropwise added to the mixture over 1 hour with stirring. Then, the mixture was returned to room temperature and stirring was continued. The reaction was traced by sampling the reaction mixture and carrying out a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 16.5 g of a polyfunctional acrylate compound represented by the formula (1). The polyfunctional acrylate compound had a number average molecular weight of 1,705 and a weight average molecular weight of 2,298.

10 g of the polyfunctional acrylate compound was molten, degassed and molded at 150° C. and then cured at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 2,000 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Example 7

(Synthesis of Bifunctional PPE Oligomer Compound)

A longitudinally long reactor having a volume of 2 liters and equipped with a stirrer, a thermometer, an air-introducing tube and baffleplates was charged with 1.3 g (0.012 mol) of CuCl, 70.7 g (0.55 mol) of di-n-butylamine and 400 g of methyl ethyl ketone. The components were stirred at a reaction temperature of 40° C. A solution of 68.8 g (0.16 mol) of 4,4'-[1,4-phenylenebis (1-methylethylidene)]bis (2,3,6-trimethylphenol) as a bivalent phenol and 58.6 g (0.48 mol) of 2,6-dimehtylphenol in 800 g of methyl ethyl ketone was dropwise added to the mixture in the reactor over 120 minutes while carrying out bubbling with 2L/min of air. After the completion of the addition, stirring was carried out for 60 minutes while continuing the bubbling with 2L/min of air. A disodium dihydrogen ethylenediamine tetraacetate aqueous solution was added to the stirred mixture to terminate the reaction. Then, washing was carried out with 1N hydrochloric acid aqueous solution and then washing was carried out with pure water. The thus-obtained solution was concentrated by an evaporator and then dried under reduced pressure, to obtain 114.6 g of a bifunctional phenylene ether oligomer. The oligomer had a number average molecular weight of 934, a weight average molecular weight of 1,223 and a hydroxyl group equivalent of 496.

(Synthesis of Epoxy Compound)

A reactor equipped with a stirrer, a thermometer and a dropping funnel was heated up to 100° C. and charged with 54.6 g (hydroxyl group 0.11 mol) of the above oligomer and 292 g of epichlorohydrin. Then, a solution obtained by dissolving 8.6 g (0.13 mol) of sodium ethoxide in 30 g of ethanol was dropwise added from the dropping funnel over 60 minutes. After the completion of the addition, stirring was further carried out for 5 hours. Then, washing was carried out with pure water, and further a filtration was carried out, to remove a generated salt and impurities. Excess epichlorohydrin was distilled off from the obtained solution, and drying under reduced pressure was carried out, to obtain 56.9 g of an epoxy compound represented by the formula (9). According to an IR analysis of the obtained epoxy compound, the absorption peak (3,600 cm−1) of a phenolic hydroxyl group disappeared, and according to a NMR analysis, a peak derived from glycidyl ether appeared, so that it was confirmed that all functional groups were changed. The epoxy compound had a number average molecular weight of 1,092, a weight average molecular weight of 1,408 and an epoxy equivalent of 612.

(Synthesis of Epoxy Acrylate Compound)

A reactor equipped with a stirrer, a thermometer and a reflux tube was charged with 28.1 g of the above epoxy compound, 3.3 g of an acrylic acid, 20 g of toluene, 0.13 g of triphenylphosphine and 13 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 40 g of toluene. The diluted reaction solution was dropwise added to methanol to obtain a precipitate. A solid was recovered by a filtration and then the recovered solid was dried under reduced pressure to obtain 28.3 g of an epoxy acrylate compound. The epoxyacrylate compound had a number average molecular weight of 1,497 and a weight average molecular weight of 1,841.

(Synthesis of Polyfunctional Acrylate Compound)

A reactor equipped with a stirrer, a thermometer and a dropping funnel was charged with 25 g of the above epoxy acrylate compound, 4.8 g of triethylamine and 400 g of methylene chloride. 4.3 g of acryloyl chloride and 100 g of methylene chloride were placed in the dropping funnel. The mixture in the reactor was cooled down to 0° C. under nitrogen atmosphere and the acryloyl chloride was dropwise added to the mixture over 1 hour with stirring. Then, the mixture was returned to room temperature and stirring was continued. The reaction was traced by sampling the reaction mixture and carrying out a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 17.6 g of a polyfunctional acrylate compound represented by the formula (1). The polyfunctional acrylate compound had a number average molecular weight of 1,788 and a weight average molecular weight of 2,407.

10 g of the polyfunctional acrylate compound was molten, degassed and molded at 150° C. and then cured at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 2,000 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Example 8
(Synthesis of Bifunctional PPE Oligomer Compound)

A longitudinally long reactor having a volume of 2 liters and equipped with a stirrer, a thermometer, an air-introducing tube and baffleplates was charged with 1.3 g (0.012 mol) of CuCl, 70.7 g (0.55 mol) of di-n-butylamine and 400 g of methyl ethyl ketone. The components were stirred at a reaction temperature of 40° C. A solution of 41.0 g (0.16 mol) of 4,4'-methylenebis (2,6-dimethylphenol) as a bivalent phenol and 58.6 g (0.48 mol) of 2,6-dimehtylphenol in 800 g of methyl ethyl ketone was dropwise added to the mixture in the reactor over 120 minutes while carrying out bubbling with 2L/min of air. After the completion of the addition, stirring was carried out for 60 minutes while continuing the bubbling with 2L/min of air. A disodium dihydrogen ethylenediamine tetraacetate aqueous solution was added to the stirred mixture to terminate the reaction. Then, washing was carried out with 1N hydrochloric acid aqueous solution and then washing was carried out with pure water. The thus-obtained solution was concentrated by an evaporator and then dried under reduced pressure, to obtain 94.6 g of a bifunctional phenylene ether oligomer. The oligomer had a number average molecular weight of 801, a weight average molecular weight of 1,081 and a hydroxyl group equivalent of 455.

(Synthesis of Epoxy Compound)

A reactor equipped with a stirrer, a thermometer and a dropping funnel was heated up to 100° C. and charged with 50.1 g (hydroxyl group 0.11 mol) of the above oligomer and 292 g of epichlorohydrin. Then, a solution obtained by dissolving 8.6 g (0.13 mol) of sodium ethoxidein 30 g of ethanol was dropwise added from the dropping funnel over 60 minutes. After the completion of the addition, stirring was further carried out for 5 hours. Then, washing was carried out with pure water and further a filtration was carried out, to remove a generated salt and impurities. Excess epichlorohydrin was distilled off from the obtained solution, and drying under reduced pressure was carried out, to obtain 50.2 g of an epoxy compound represented by the formula (9). According to an IR analysis of the obtained epoxy compound, the absorption peak (3,600 cm−1) of a phenolic hydroxyl group disappeared, and according to a NMR analysis, a peak derived from glycidyl ether appeared, so that it was confirmed that all functional groups were changed. The epoxy compound had a number average molecular weight of 956, a weight average molecular weight of 1,204 and an epoxy equivalent of 545.

(Synthesis of Epoxy Acrylate Compound)

A reactor equipped with a stirrer, a thermometer and a reflux tube was charged with 25.1 g of the above epoxy compound, 3.3 g of an acrylic acid, 20 g of toluene, 0.13 g of triphenylphosphine and 13 mg of hydroquinone methyl ether. The mixture was heated up to 120° C. and allowed to react with stirring. During the reaction, an acid value was measured and the reaction was continued until the acid value became 2 mgKOH/g. The stirring time at 120° C. was 5 hours. The reaction solution was diluted with 40 g of toluene. The diluted reaction solution was dropwise added to methanol to obtain a precipitate. A solid was recovered by a filtration and then the recovered solid was dried under reduced pressure to obtain 25.4 g of an epoxy acrylate compound. The epoxy acrylate compound had a number average molecular weight of 1,359 and a weight average molecular weight of 1,657.

(Synthesis of Polyfunctional Acrylate Compound)

A reactor equipped with a stirrer, a thermometer and a dropping funnel was charged with 25 g of the above epoxy acrylate compound, 5.3 g of triethylamine and 400 g of methylene chloride. 4.8 g of acryloyl chloride and 100 g of methylene chloride were placed in the dropping funnel. The mixture in the reactor was cooled down to 0° C. under nitrogen atmosphere and the acryloyl chloride was dropwise added to the mixture over 1 hour with stirring. Then, the mixture was returned to room temperature and stirring was continued. The reaction was traced by sampling the reaction mixture and carrying out a NMR measurement. The reaction was terminated after 2-hours stirring. Then, washing was carried out with a 0.1 N hydrochloric acid aqueous solution and pure water. An organic layer was concentrated and then dropwise added to methanol to obtain a precipitate. A solid was recovered by filtration and the recovered solid was dried under reduced pressure to obtain 16.6 g of a polyfunctional acrylate compound represented by the formula (1). The polyfunctional acrylate compound had a number average molecular weight of 1,623 and a weight average molecular weight of 2,278.

10 g of the polyfunctional acrylate compound was molten, degassed and molded at 150° C. and then cured at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 2,000 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product. A pencil mar strength (JIS K5400) of the resin cured product was H.

Comparative Example 2

10 g of the same epoxy acrylate compound as that obtained in Example 4 was degassed and molded at 150° C. and then thermally cured at 200° C. for 6 hours to obtain a cured product.

The cured products obtained in Examples 4 to 8 and Comparative Example 2 were evaluated for properties.

Table 2 shows evaluation results.

TABLE 2

|  | Ex. 4 Cured product | Ex. 5 Cured product | Ex. 6 Cured product | Ex. 7 Cured product | Ex. 8 Cured product | CEx. 2 Cured product |
| --- | --- | --- | --- | --- | --- | --- |
| Tg (° C.) | 224 | 225 | 223 | 230 | 235 | 182 |
| Dielectric constant (1 GHz) | 2.74 | 2.77 | 2.76 | 2.74 | 2.71 | 2.81 |
| Dielectric loss tangent (1 GHz) | 0.013 | 0.012 | 0.011 | 0.012 | 0.011 | 0.025 |

Ex. = Example,
CEx. = Comparative Example

Example 9

(Synthesis of Bifunctional Phenylene Ether Oligomer Compound)

A longitudinally long reactor having a volume of 12 liters and equipped with a stirrer, a thermometer, an air-introducing tube and baffleplates was charged with 3.88 g (17.4 mmol) of $CuBr_2$, 0.75 g (4.4 mmol) of N,N'-di-t-butylethylenediamine, 28.04 g (277.6 mmol) of n-butyldimethylamine and 2,600 g of toluene. The components were stirred at a reaction temperature of 40° C. A mixed solution of 129.32 g (0.48 mol) of 2,2',3,3',5,5'-hexamethyl-(1,1'-biphenyl)-4,4'-diol, 292.19 g (2.40 mol) of 2,6-dimehtylphenol, 0.51 g (2.9 mmol) of N,N'-di-t-butylethylenediamine and 10.90 g (108.0 mmol) of n-butyldimethylamine in 2,300 g of methanol was dropwise added to the mixture in the reactor over 230 minutes while carrying out bubbling with 5.2L/min of a mixed gas of nitrogen and air which gas had an oxygen content of 8%. Stirring was carried out. After the completion of the addition, 1,500 g of water in which 19.89 g (52.3 mmol) of tetrasodium ethylenediamine tetraacetate was dissolved was added to the stirred mixture to terminate the reaction. Then, an organic layer was washed with 1N hydrochloric acid aqueous solution and then washed with pure water. The thus-obtained solution was concentrated by an evaporator to obtain 833.40 g of a 50 wt % solution of a bifunctional phenylene ether oligomer. The oligomer had a number average molecular weight of 930, a weight average molecular weight of 1,460 and a hydroxyl group equivalent of 465.

(Synthesis of Epoxy Compound)

A reactor equipped with a stirrer, a thermometer and a dropping funnel was heated up to 100° C. and charged with 560 g (hydroxyl group 0.60 mol) of the above 50 wt % solution of oligomer and 1,599 g of epichlorohydrin. Then, 237.60 g (0.72 mol) of an ethanol solution of sodium ethoxide (20.7 wt %; supplied by Nippon Soda Co., Ltd.) was dropwise added from the dropping funnel over 60 minutes. After the completion of the addition, stirring was further carried out for 5 hours. Then, washing was carried out with pure water and further a filtration was carried out, to remove a generated salt and impurities. Excess epichlorohydrin was distilled off from the obtained solution, and drying under reduced pressure was carried out, to obtain 316.10 g of an epoxy compound. According to an IR analysis of the obtained epoxy compound, the absorption peak (3,600 cm−1) of a phenolic hydroxyl group disappeared, and according to a $^1$H-NMR analysis, a peak derived from glycidyl ether appeared, so that it was confirmed that all functional groups were changed. The epoxy compound had a number average molecular weight of 960, a weight average molecular weight of 1,205 and an epoxy equivalent of 520.

(Synthesis of Epoxy Acrylate Compound)

A reactor equipped with a stirrer, a thermometer and a reflux tube was charged with 300.08 g (0.58 mol) of the above epoxy compound, 49.89 g (0.69 mol) of an acrylic acid, 330.57 g of toluene, 1.50 g of triethylamine and 0.30 g of hydroquinone methyl ether. The mixture was heated up to 120° C. and allowed to react with stirring. During the reaction, an acid value was measured and the reaction was continued until the acid value became 9 mgKOH/g. The stirring time at 120° C. was 10 hours. A 50 wt % solution of an epoxy acrylate compound was obtained. The epoxy acrylate compound had a number average molecular weight of 1,405 and a weight average molecular weight of 1,995.

(Synthesis of Polyfunctional Acrylate Compound)

A reactor equipped with a stirrer, a thermometer and a dropping funnel was charged with 120.05 g of the above 50 wt % solution of epoxy acrylate compound, 15.30 g (0.15 mol) of triethylamine and 500 g of methylene chloride. 21.20 g (0.15 mol) of benzoyl chloride and 170 g of methylene chloride were placed in the dropping funnel. The mixture in the reactor was cooled down to 0° C. under nitrogen atmosphere and the benzoyl chloride was dropwise added to the mixture over 1 hour with stirring. Then, the mixture was returned to room temperature and stirring was continued. The reaction mixture was sampled and the reaction was traced by a NMR measurement. The reaction was terminated after 2-hours stirring. Then, washing was carried out with a 0.1 N hydrochloric acid aqueous solution and pure water. An organic layer was concentrated and then dropwise added to methanol to carry out solidification. A solid was recovered by filtration and the recovered solid was dried under reduced pressure to obtain 59.07 g of a polyfunctional acrylate compound. The polyfunctional acrylate compound had a number average molecular weight of 1,840 and a weight average molecular weight of 2,425. 10 g of the polyfunctional acrylate compound was molten, degassed and molded at 150° C. and then cured under heat at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 1,500 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product.

Example 10

(Synthesis of Bifunctional Phenylene Ether Oligomer Compound)

A longitudinally long reactor having a volume of 12 liters and equipped with a stirrer, a thermometer, an air-introducing tube and baffleplates was charged with 2.77 g (12.5 mmol) of $CuBr_2$, 0.54 g (3.1 mmol) of N,N'-di-t-butylethylenediamine, 20.03 g (198.3 mmol) of n-butyldimethylamine and 2,600 g of toluene. The components were stirred at a reaction temperature of 40° C. A mixed solution of 155.18 g (0.48 mol) of 4,4'-cyclohexylidenebis(2,6-dimethylphenol) as phenol, 175.31 g (1.44 mol) of 2,6-dimehtylphenol, 0.36 g (2.1 mmol) of N,N'-di-t-butylethylenediamine and 7.79 g (77.1 mmol) of n-butyldimethylamine in 2,300 g of methanol was dropwise added to the mixture in the reactor over 230 minutes while carrying out bubbling with 5.2L/min of a mixed gas of nitrogen and air which gas had an oxygen content of 8%. Stirring was carried out. After the completion of the addition, 1,500 g of water in which 14.20 g (37.4 mmol) of tetrasodium ethylenediamine tetraacetate was dissolved was added to the stirred mixture to terminate the reaction. Then, an organic layer was washed with 1N hydrochloric acid aqueous solution and then washed with pure water. The thus-obtained solution was concentrated by an evaporator to obtain 655.22 g of a 50 wt % solution of a bifunctional phenylene ether oligomer. The oligomer had a number average molecular weight of 655, a weight average molecular weight of 940 and a hydroxyl group equivalent of 335.

(Synthesis of Epoxy Compound)

A reactor equipped with a stirrer, a thermometer and a dropping funnel was heated up to 100° C. and charged with 560 g (hydroxyl group 0.84 mol) of the above 50 wt % solution of oligomer and 2,219.8 g of epichlorohydrin. Then, 329.80 g (1.00 mol) of an ethanol solution of sodium ethoxide (20.7 wt %; supplied by Nippon Soda Co., Ltd.) was dropwise added from the dropping funnel over 60 minutes. After the completion of the addition, stirring was further carried out for 5 hours. Then, washing was carried out with pure water and further a filtration was carried out, to remove a generated salt and impurities. Excess epichlorohydrin was distilled off from the obtained solution, and drying under reduced pressure was carried out, to obtain 327.90 g of an epoxy compound. According to an IR analysis of the obtained epoxy compound, the absorption peak (3,600 cm–1) of a phenolic hydroxyl group disappeared, and according to a $^1$H-NMR analysis, a peak derived from glycidyl ether appeared, so that it was confirmed that all functional groups were changed. The epoxy compound had a number average molecular weight of 710, a weight average molecular weight of 915 and an epoxy equivalent of 370.

(Synthesis of Epoxy Acrylate Compound)

A reactor equipped with a stirrer, a thermometer and a reflux tube was charged with 300.03 g (0.81 mol) of the above epoxy compound, 70.11 g (0.97 mol) of an acrylic acid, 344.43 g of toluene, 1.50 g of triethylamine and 0.30 g of hydroquinone methyl ether. The mixture was heated up to 120° C. and allowed to react with stirring. During the reaction, an acid value was measured and the reaction was continued until the acid value became 12 mgKOH/g. The stirring time at 120° C. was 10 hours. A 50 wt % solution of an epoxy acrylate compound was obtained. The epoxy acrylate compound had a number average molecular weight of 1,135 and a weight average molecular weight of 1,550.

(Synthesis of Polyfunctional Acrylate Compound)

A reactor equipped with a stirrer, a thermometer and a dropping funnel was charged with 120.03 g of the above 50 wt % solution of epoxy acrylate compound, 20.60 g (0.20 mol) of triethylamine and 500 g of methylene chloride. 28.690 g (0.20 mol) of benzoyl chloride and 200 g of methylene chloride were placed in the dropping funnel. The mixture in the reactor was cooled down to 0° C. under nitrogen atmosphere and the benzoyl chloride was dropwise added to the mixture over 1 hour with stirring. Then, the mixture was returned to room temperature and stirring was continued. The reaction mixture was sampled and the reaction was traced by a $^1$H-NMR measurement. The reaction was terminated after 2-hours stirring. Then, washing was carried out with a 0.1 N hydrochloric acid aqueous solution and pure water. An organic layer was concentrated and then dropwise added to methanol to carry out solidification. A solid was recovered by filtration and the recovered solid was dried under reduced pressure to obtain 62.65 g a polyfunctional acrylate compound. The polyfunctional acrylate compound had a number average molecular weight of 1,600 and a weight average molecular weight of 2,050. 10 g of the polyfunctional acrylate compound was molten, degassed and molded at 150° C. and then cured under heat at 200° C. for 6 hours to obtain a cured product.

6 g of the polyfunctional acrylate compound was dissolved in 4 g of carbitol acetate and 0.6 g of Darocur 1173 (supplied by Ciba Specialty Chemicals, photopolymerization initiator) was added to the resultant solution to obtain a resin composition. The resin composition was applied to a copper-clad laminate surface with a screen-printing machine and then dried with an air dryer at 80° C. for 60 minutes. Then a pattern film was placed thereon and the copper-clad laminate surface was exposed at 1,500 mJ using a UV irradiation device (supplied by EYE GRAPHICS Co., Ltd.: UB0151, light source: metal halide lamp). After the exposure, development was carried out with methyl ethyl ketone. In this case, only non-exposed portions were dissolved in the methyl ethyl ketone, to obtain a development pattern of a resin cured product.

Comparative Example 3

10 g of a bisphenol A type epoxy acrylate (SP4509: supplied by SHOWA HIGHPOLYMER CO., LTD) was molten, degassed and molded at 120° C. and then cured under heat at 200° C. for 6 hours to obtain a cured product.

Comparative Example 4

10 g of novolak type epoxy acrylate (SP4010, supplied by SHOWA HIGHPOLYMER CO., LTD) was molten, degassed and molded at 120° C. and then cured under heat at 200° C. for 6 hours to obtain a cured product.

The cured products obtained in Examples 9 and 10 and Comparative Examples 3 and 4 were evaluated for properties. Table 3 shows evaluation results.

TABLE 3

|  | Example 9 Cured product | Example 10 Cured product | Comparative Example 3 Cured product | Comparative Example 4 Cured product |
|---|---|---|---|---|
| Tg (° C.) | 175 | 160 | 140 | 142 |
| Dielectric constant (1 GHz) | 2.65 | 2.66 | 3.31 | 3.1 |
| Dielectric loss tangent (1 GHz) | 0.008 | 0.009 | 0.052 | 0.032 |

What is claimed is:

1. A (meth)acrylate compound represented by the formula (1) or the formula (2),

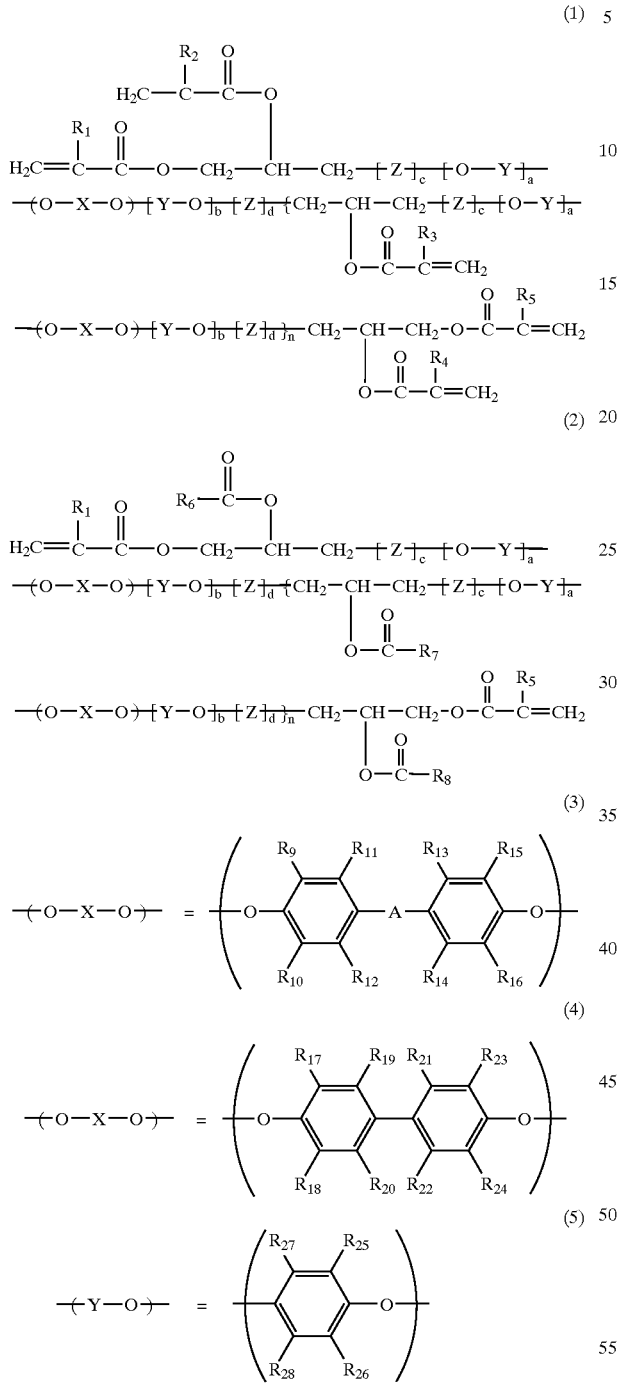

wherein each of $R_1$, $R_2$, $R_3$, $R_4$ and $R_5$ is independently a hydrogen atom or a methyl group, each of $R_6$, $R_7$ and $R_8$ is independently a linear, branched or cyclic hydrocarbon having 20 or less carbon atoms, —(O—X—O)— is represented by the formula (3) (in which A is a linear, branched or cyclic hydrocarbon having 20 or less carbon atoms, each of $R_9$, $R_{10}$, $R_{15}$ and $R_{16}$ is independently a halogen atom, an alkyl group having 6 or less carbon atoms or a phenyl group and each of $R_{11}$, $R_{12}$, $R_{13}$ and $R_{14}$ is independently a hydrogen atom, a halogen atom, an alkyl group having 6 or less carbon atoms or a phenyl group) or the formula (4) (in which each of $R_{17}$, $R_{18}$, $R_{19}$, $R_{23}$ and $R_{24}$ is independently a halogen atom, an alkyl group having 6 or less carbon atoms or a phenyl group and each of $R_{20}$, $R_{21}$ and $R_{22}$ is independently a hydrogen atom, a halogen atom, an alkyl group having 6 or less carbon atoms or a phenyl group), —(Y—O)— is an arrangement of one kind of structure defined by the formula (5) or a random arrangement of at least two kinds of structures defined by the formula (5) (in which each of $R_{25}$ and $R_{26}$ is independently a halogen atom, an alkyl group having 6 or less carbon atoms or a phenyl group and each of $R_{27}$ and $R_{28}$ is independently a hydrogen atom, a halogen atom, an alkyl group having 6 or less carbon atoms or a phenyl group), Z is an organic group which has at least one carbon atom and which may contain an oxygen atom, a nitrogen atom, a sulfur atom or a halogen atom, each of a and b is an integer of 0 to 30, provided that at least either a or b is not 0, each of c and d is an integer of 0 or 1, and n is an integer of 0 to 10.

2. A (meth)acrylate compound according to claim 1, wherein $R_9$, $R_{10}$, $R_{15}$ and $R_{16}$ in —(O—X—O)— of the formula (3) are an alkyl group having 3 or less carbon atoms, $R_{11}$, $R_{12}$, $R_{13}$ and $R_{14}$ in —(O—X—O)— of the formula (3) are a hydrogen atom or an alkyl group having 3 or less carbon atoms, $R_{25}$ and $R_{26}$ in —(Y—O)— of the formula (5) are an alkyl group having 3 or less carbon atoms and $R_{27}$ and $R_{28}$ in —(Y—O)— of the formula (5) are a hydrogen atom or an alkyl group having 3 or less carbon atoms.

3. A (meth)acrylate compound according to claim 1, wherein $R_{17}$, $R_{18}$, $R_{19}$, $R_{23}$ and $R_{24}$ in —(O—X—O)— of the formula (4) are an alkyl group having 3 or less carbon atoms, $R_{20}$, $R_{21}$ and $R_{22}$ in —(O—X—O)— of the formula (4) are a hydrogen atom or an alkyl group having 3 or less carbon atoms, $R_{25}$ and $R_{26}$ in —(Y—O)— of the formula (5) are an alkyl group having 3 or less carbon atoms and $R_{27}$ and $R_{28}$ in —(Y—O)— of the formula (5) are a hydrogen atom or an alkyl group having 3 or less carbon atoms.

4. A (meth)acrylate compound according to claim 1, wherein —(O—X—O)— is represented by the formula (3) or the formula (4) and —(Y—O)— is an arrangement of the formula (7) or the formula (8) or a random arrangement of the formula (7) and the formula (8),

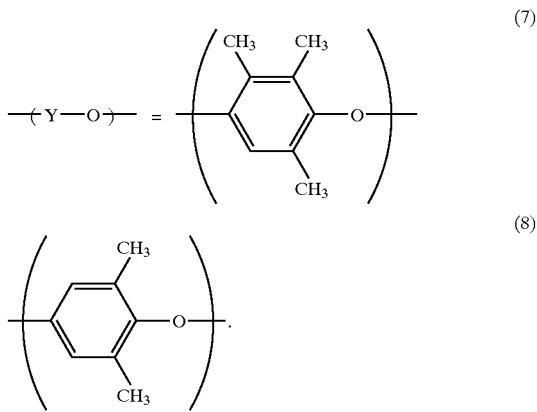

5. A (meth)acrylate compound according to claim 1, wherein —(O—X—O)— is represented by the formula (6) and —(Y—O)— is represented by the formula (5),

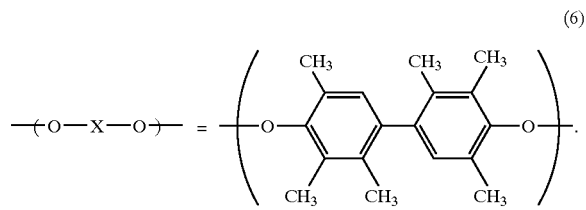

6. A (meth)acrylate compound according to claim 1, wherein —(O—X—O)— is represented by the formula (6) and —(Y—O)— is represented by the formula (7) or the formula (8).

7. A curable resin composition containing the (meth) acrylate compound as recited in claim 1.

8. A photosensitive resin composition containing the (meth)acrylate compound as recited in claim 1 and a photopolymerization initiator.

9. A cured product obtained by curing the curable resin composition as recited in claim 7 or the photosensitive resin composition as recited in claim 8.

* * * * *